(12) United States Patent
Ostroverkhov et al.

(10) Patent No.: US 10,070,796 B2
(45) Date of Patent: Sep. 11, 2018

(54) SYSTEMS AND METHODS FOR QUANTITATIVE MICROCIRCULATION STATE MONITORING

(71) Applicant: General Electric Company, Schenectady, NY (US)

(72) Inventors: Victor Petrovich Ostroverkhov, Ballston Lake, NY (US); Alberto Santamaria-Pang, Niskayuna, NY (US); Dmitry V. Dylov, Niskayuna, NY (US); Ali Can, Niskayuna, NY (US); Siavash Yazdanfar, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 345 days.

(21) Appl. No.: 14/614,026

(22) Filed: Feb. 4, 2015

(65) Prior Publication Data
US 2016/0220129 A1 Aug. 4, 2016

(51) Int. Cl.
*A61B 5/026* (2006.01)
*A61B 5/02* (2006.01)
*A61B 5/00* (2006.01)

(52) U.S. Cl.
CPC ........ *A61B 5/0261* (2013.01); *A61B 5/02007* (2013.01); *A61B 5/6815* (2013.01); *A61B 2562/0238* (2013.01); *A61B 2576/00* (2013.01)

(58) Field of Classification Search
CPC . A61B 5/02007; A61B 5/0261; A61B 5/6815; A61B 2562/0238; A61B 2576/00
USPC ...................................................... 600/479
See application file for complete search history.

(56) References Cited

U.S. PATENT DOCUMENTS

| | | | |
|---|---|---|---|
| 5,991,697 A | 11/1999 | Nelson et al. | |
| 7,113,817 B1 * | 9/2006 | Winchester, Jr. .... | A61B 3/1233 356/27 |
| 7,282,346 B2 * | 10/2007 | Fruehauf .......... | G01N 33/57484 435/4 |
| 7,496,395 B2 | 2/2009 | Serov et al. | |

(Continued)

FOREIGN PATENT DOCUMENTS

WO 20110070357 A1 6/2011

OTHER PUBLICATIONS

Angus et al., "Epidemiology of Severe Sepsis in the United States: Analysis of Incidence, Outcome, and Associated Costs of Care", Critical Care Medicine, vol. No. 29, Issue No. 7, pp. 1303-1310, 2001.

(Continued)

*Primary Examiner* — Christopher A Flory
(74) *Attorney, Agent, or Firm* — GE Global Patent Operation; Pabitra Chakrabarti

(57) ABSTRACT

A method in one embodiment includes acquiring optical image information with a detection unit configured to be operably coupled to a patient. The optical image information corresponds to microcirculation of the patient. The method also includes generating a microcirculation map of microvasculature of the patient using the optical image information. Further, the method includes generating a quantitative microcirculation index based on the microcirculation map, the quantitative microcirculation index corresponding to a condition of the patient.

20 Claims, 9 Drawing Sheets

(56) References Cited

U.S. PATENT DOCUMENTS

| | | | |
|---|---|---|---|
| 7,745,155 B2* | 6/2010 | Lin | A61K 49/0032 422/73 |
| 8,178,342 B2* | 5/2012 | Lin | A61K 49/0032 422/68.1 |
| 8,211,660 B2* | 7/2012 | Lin | A61K 49/0032 422/73 |
| 8,574,859 B2* | 11/2013 | Lin | A61B 5/0059 422/68.1 |
| 8,708,909 B2* | 4/2014 | Goertz | A61K 49/223 600/407 |
| 8,961,932 B2* | 2/2015 | Silverman | A61B 5/0261 424/9.1 |
| 9,289,128 B2* | 3/2016 | Lin | A61B 5/0059 |
| 9,351,642 B2* | 5/2016 | Nadkarni | A61B 5/0059 |
| 9,510,758 B2* | 12/2016 | Warger, II | A61B 5/0066 |
| 2002/0039754 A1* | 4/2002 | Fruehauf | G01N 33/57484 435/7.23 |
| 2006/0039935 A1* | 2/2006 | Antosh | A61K 9/0014 424/401 |
| 2006/0078501 A1* | 4/2006 | Goertz | A61K 49/223 424/9.52 |
| 2006/0247514 A1* | 11/2006 | Panasyuk | A61B 5/0059 600/410 |
| 2007/0016079 A1* | 1/2007 | Freeman | A61B 5/0059 600/476 |
| 2007/0038042 A1* | 2/2007 | Freeman | A61B 5/14551 600/310 |
| 2007/0098134 A1* | 5/2007 | Toyoshima | A61B 6/032 378/4 |
| 2007/0232930 A1* | 10/2007 | Freeman | A61B 5/0059 600/476 |
| 2008/0171944 A1* | 7/2008 | Brenneman | A61B 17/11 600/509 |
| 2008/0241199 A1* | 10/2008 | Silverman | A61B 5/0261 424/400 |
| 2008/0262327 A1* | 10/2008 | Kato | A61B 5/14553 600/324 |
| 2009/0118622 A1 | 5/2009 | Durkin et al. | |
| 2009/0328239 A1* | 12/2009 | Brauner | A61B 6/032 800/3 |
| 2010/0027857 A1* | 2/2010 | Wang | A61B 3/102 382/128 |
| 2010/0104168 A1 | 4/2010 | Dobbe | |
| 2010/0159497 A1* | 6/2010 | Kimia | G06T 7/0012 435/29 |
| 2010/0304424 A1 | 12/2010 | Vink et al. | |
| 2011/0033091 A1* | 2/2011 | Fujii | A61B 3/1225 382/117 |
| 2011/0044929 A1* | 2/2011 | Reddington | A61K 9/0024 424/78.3 |
| 2011/0046888 A1* | 2/2011 | Skobeltsina | G01N 33/574 702/19 |
| 2011/0103657 A1* | 5/2011 | Kang | G06T 7/74 382/128 |
| 2011/0169978 A1 | 7/2011 | Lasser et al. | |
| 2011/0319775 A1 | 12/2011 | Fujii et al. | |
| 2012/0063665 A1* | 3/2012 | Wang | A61B 5/0066 382/134 |
| 2012/0095354 A1 | 4/2012 | Dunn et al. | |
| 2012/0150048 A1* | 6/2012 | Kang | A61B 6/508 600/481 |
| 2012/0162438 A1 | 6/2012 | Thakor et al. | |
| 2012/0190967 A1 | 7/2012 | Nahm | |
| 2012/0269420 A1* | 10/2012 | Najarian | A61B 5/02007 382/134 |
| 2013/0245455 A1* | 9/2013 | Freeman | A61B 5/0059 600/473 |
| 2013/0245456 A1* | 9/2013 | Ferguson, Jr. | A61B 5/0059 600/473 |
| 2013/0301008 A1* | 11/2013 | Srivastava | G01B 9/02083 351/246 |
| 2014/0031647 A1* | 1/2014 | Lin | A61B 5/0059 600/317 |
| 2014/0073917 A1* | 3/2014 | Huang | A61B 5/0066 600/427 |
| 2014/0112559 A1* | 4/2014 | Freeman | A61B 5/0059 382/128 |
| 2014/0188028 A1* | 7/2014 | Brenneman | A61B 17/11 604/8 |
| 2014/0194711 A1 | 7/2014 | Al-Ali | |
| 2014/0257113 A1* | 9/2014 | Panasyuk | A61B 5/0075 600/476 |
| 2014/0288419 A1* | 9/2014 | Wang | A61B 5/0066 600/425 |
| 2014/0294235 A1* | 10/2014 | Ishida | G06K 9/0061 382/103 |
| 2014/0357990 A1* | 12/2014 | Wang | A61B 5/0261 600/425 |
| 2015/0073271 A1* | 3/2015 | Lee | A61B 5/0261 600/427 |
| 2015/0119705 A1* | 4/2015 | Tochterman | A61B 5/02158 600/425 |
| 2015/0190090 A1* | 7/2015 | Silverman | A61K 31/04 600/363 |
| 2015/0287183 A1* | 10/2015 | Kang | G06T 7/74 382/128 |
| 2015/0302584 A1* | 10/2015 | Brauner | A61B 6/508 382/128 |
| 2015/0348287 A1* | 12/2015 | Yi | G06T 11/003 382/131 |
| 2015/0374241 A1* | 12/2015 | Vallee | A61B 5/14551 600/301 |
| 2016/0058307 A1* | 3/2016 | Svanerudh | A61B 5/7278 600/427 |
| 2016/0066798 A1* | 3/2016 | Wang | G06T 7/0012 600/425 |
| 2016/0113507 A1* | 4/2016 | Reza | G01N 21/1717 356/477 |
| 2016/0128889 A1* | 5/2016 | Sackner | A61H 1/005 601/29 |
| 2016/0157737 A1* | 6/2016 | Huang | A61B 5/0066 600/425 |
| 2016/0220129 A1* | 8/2016 | Ostroverkhov | A61B 5/0261 |
| 2016/0239956 A1* | 8/2016 | Kang | G06T 17/005 |
| 2016/0310023 A1* | 10/2016 | Chachisvilis | A61B 5/0053 |
| 2016/0317029 A1* | 11/2016 | Srivastava | G01B 9/02083 |
| 2016/0331229 A1* | 11/2016 | Huang | A61B 5/0066 |
| 2016/0367145 A1* | 12/2016 | Lasser | A61B 3/1233 |
| 2017/0024882 A1* | 1/2017 | Kang | G06K 9/6215 |

OTHER PUBLICATIONS

Backer et al., "How to Evaluate the Microcirculation: Report of a Round Table Conference", Critical Care, vol. No. 11, Issue No. 5, pp. 1-9, 2007.

Shapiro et al., "Skin Biopsies Demonstrate Site-Specific Endothelial Activation in Mouse Models of Sepsis", Journal of Vascular Research, vol. No. 46, Issue No. 5, pp. 495-502, Apr. 4, 2009.

Boas et al., "Laser Speckle Contrast Imaging in Biomedical Optics", Journal of Biomedical Optics, vol. No. 15, Issue No. 1, pp. 011109-1-011109-12, Jan. / Feb. 2010.

Wu et al., "A Hybrid De-Noising Method on LASCA Images of Blood Vessels", Journal of Signal and Information Processing, vol. No. 3, Issue No. 1, pp. 92-97, Feb. 2012.

Nadort et al., "Quantitative Laser Speckle Flowmetry of the in Vivo Microcirculation using Sidestream Dark Field Microscopy", Biomedical Optics Express, vol. No. 4, Issue No. 11, pp. 2347-2361, Nov. 1, 2013.

\* cited by examiner

SYSTEMS AND METHODS FOR QUANTITATIVE MICROCIRCULATION STATE MONITORING

BACKGROUND

Microcirculation, or the process of delivery of fresh blood to organ tissue through the network of the smallest blood vessels, provides a supply of nutrients and oxygen to the tissue, and removal of byproducts of metabolism. Accordingly, the state of microcirculation may be an indicator of tissue vitality. Various clinical conditions (e.g., stroke, traumatic shock, or sepsis, among others) may result in altered or disrupted microcirculation, which, if untreated in a timely manner, may result in tissue damage and/or other adverse results. For example, in sepsis and septic shock, microvascular blood flow may be altered in a noticeable fashion that may be correlated with clinical outcome.

Severe sepsis, for example, affects around a million patients annually in the United States, with a mortality rate of about 30-50%. However, there is no conventional, widely accepted technology that has high accuracy sepsis detection while being fast, non-invasive, and integrated into a clinical workflow.

BRIEF DESCRIPTION

In one embodiment, a method includes acquiring optical image information with a detection unit configured to be operably coupled to a patient. The optical image information corresponds to microcirculation of the patient. The method also includes generating a microcirculation map of microvasculature of the patient using the optical image information. Further, the method includes generating a quantitative microcirculation index based on the microcirculation map, the quantitative microcirculation index corresponding to a condition of the patient.

In another embodiment, a system is provided that includes a detection unit and at least one processing unit. The detection unit is configured to be operably coupled to a patient and to acquire optical image information corresponding to microcirculation of the patient. The at least one processing unit is configured to be operably coupled to the detection unit, and configured to generate a microcirculation map of microvasculature of the patient using the optical image information, and to generate a quantitative microcirculation index based on the microcirculation map, the quantitative microcirculation index corresponding to a condition of the patient.

In another embodiment, a tangible and non-transitory computer readable medium includes one or more computer software modules configured to direct one or more processors to acquire optical image information via a detection unit configured to be operably coupled to a patient, with the optical image information corresponding to microcirculation of the patient; generate a microcirculation map of microvasculature of the patient using the optical image information; and generate a quantitative microcirculation index based on the microcirculation map, the quantitative microcirculation index corresponding to a condition of the patient.

DETAILED DESCRIPTION

Figure 1:
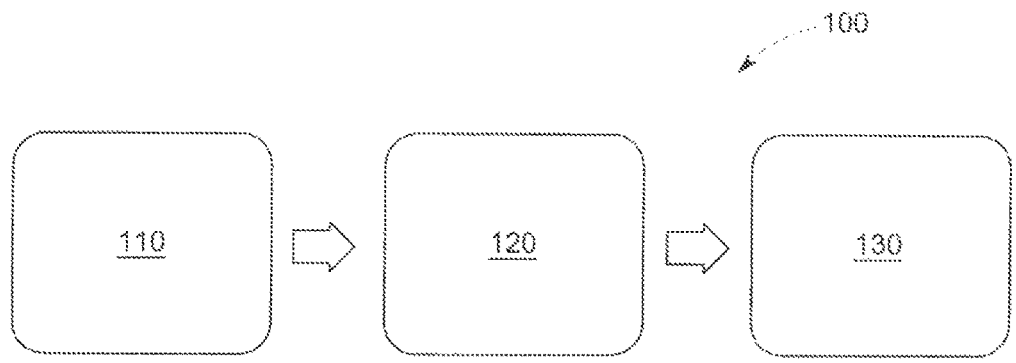
FIG. 1 is a schematic block diagram of a process flow in accordance with various embodiments.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide, for example, for continuous non-invasive monitoring of the state of microvascular blood flow (or blood perfusion) in tissue. Various embodiments provide for autonomous non-invasive monitoring, or monitoring that may be performed without intervention or participation by an operator. In various embodiments, the monitoring is achieved via analysis of an image of a blood flow map in the tissue. For example, the image may be analyzed by extracting one or more quantitative parameters from the image. The one or more quantitative parameters may be automatically determined by a processing unit configured (e.g., programmed) to identify, measure, or determine one or more aspects of mapped vessels (e.g., a diameter of one or more vessels, a ratio of diameters for different vessels, a percentage of vessels falling into one or more size ranges, a change in diameter of a vessel over time, a rate of change of a vessel measurement, or the like). The one or more parameters may be used as a predictor of onset of clinical conditions that have a disruptive effect on microcirculation (e.g., sepsis, shock, or trauma) and/or serve as a parameter to monitor progression of a disease and/or response of a patient to treatment. As used herein, microcirculation may be understood as circulation through microvasculature of a patient, and microvasculature as used herein may be understood as including capillaries as well as vessels directly connected to capillaries (e.g., arterioles, venules).

Various embodiments provide systems and/or methods for monitoring the state of microvascular blood flow in tissue by creating an image that represents a map of blood flow in the tissue and extracting one or more quantitative parameters from the image. As discussed herein, the one or more quantitative parameters may be used as a predictor of onset of clinical conditions that have a disruptive effect on microcirculation, such as sepsis. Various embodiments enable detection of homogeneity and uniformity of flow through the tissues, for example as pronounced as changes in the density of perfused vessels, flow velocity variation, and re-perfusion rate in response to occlusion or resuscitation challenge. Various embodiments combine a flow-sensitive optical modality (e.g., Laser Speckle Imaging) with image processing and analytics to provide non-invasive and continuous monitoring of the state of microvascular blood flow.

Various embodiments utilize in-vivo real-time imaging technology (e.g., Laser Speckle Imaging) for visualizing blood flow through a microvascular bed of studied tissue at a sufficiently high resolution to identify individual microvessels. In some embodiments, three steps may be performed—acquisition of a flow map image of a microvascular bed, image processing to enhance features of interest, and extraction of a quantitative index (or indices) from measured image features. For example, as part of acquisition of a flow map image, images of a tissue region of interest are collected using an optical modality with sensitivity to local blood flow. In some embodiments, a Laser Speckle Imaging approach may be utilized to image flow across tissue. As part of image processing, features from the image or image sequence that pertain to the microcirculation state of the tissue may be extracted. In various embodiments, image analysis tools (e.g., software-based techniques for automatically identifying features and/or sizes of features and/or shapes of features from one or more images) may be used to identify features by shape (e.g., various vessel sizes, vessel branching points) and/or by temporal behavior (e.g., variability of flow rate). As part of extraction of a quantitative index, information extracted from flow images may be utilized to generate a quantitative parameter that represents a certain property of the microcirculatory state of the tissues. For example, fraction of the tissue area that shows active blood flow, a number (or combined length) of perfused vessels of a certain size, distribution of perfused vessel sizes in the image, flow rate in vessels of specified size, distribution of distances among neighboring vessels, and/or variation or trending of any of these quantities in time, may be used as observable quantities for extracting one or more quantitative parameters in various embodiments. In some embodiments, information provided by a vessel enhancement filter may be used to classify each image pixel into a corresponding bin representing a specific vessel thickness (e.g., a range of thicknesses).

In various embodiments, systems for monitoring the state of microvascular flow in tissue may include an illumination unit, an imaging unit, and a processing unit. The illumination unit is configured to support a flow-sensitive measurement modality. In some embodiments, the illumination unit includes at least one coherent illumination source such as a laser, and may optionally include at least one incoherent illumination source such as LEDs at one or more wavelengths. The imaging unit is configured to produce high resolution flow-map images of vasculature. In some embodiments, the imaging unit includes an optical system which may have an optional focus adjustment and/or field of view steering mechanism and a multi-pixels sensor such as a CCD or CMOS camera. The processing unit is configured to enhance obtained flow map image features (e.g., using one or more of filtering, de-noising, edge detection, or the like), as well as to use extracted features to generate one or more quantitative indices characterizing or corresponding to the flow state of the tissue being imaged.

At least one technical effect of various embodiments includes providing convenient, ongoing, non-invasive monitoring of flow through microvasculature. At least one technical effect of various embodiments includes providing an objective index for analyzing a medical condition corresponding to microcirculation. At least one technical effect of various embodiments is reducing operator effort and involvement with monitoring a patient and/or determining presence or absence of a medical condition such as sepsis, the severity of sepsis, and/or a quantifiable measure of patient's response to treatment. At least one technical effect of various embodiments is improved consistency in monitoring microcirculation and/or reduction of the potential for operator error in monitoring microcirculation FIG. 1 is a schematic block diagram of a process flow 100 formed in accordance with various embodiments. The process flow includes a first step 110 of flow-sensitive image acquisition, a second step 120 of image processing and feature analysis, and a third step 130 of generating a quantitative index of flow state.

At 110, flow-sensitive image acquisition of a field of view (FOV) of tissue is performed. For example, images of a tissue region of interest are collected using an optical modality with sensitivity to local blood flow. Generally, for microcirculation measurement, spatial image resolution should be high enough to capture variations of flow across the tissue region occupied by neighboring vessels. Generally, the speed of image capture may be configured or selected based on the range of physiological changes that are to be monitored.

As one example, in some embodiments where local blood flow homogeneity in tissue is of interest, vessels sized between 10 to 50 micrometers may be analyzed. Spatial inhomogeneity has been observed as a signature of disrupted microcirculation during progression of sepsis. Similarly, the time response of the system may be configured to capture natural variability (both normal and abnormal) of flow patterns that occur in tissue (e.g., due to vasomotive activity, or re-perfusion after an extrinsically applied flow occlusion, as examples).

At 120, image processing and feature analysis are performed. Generally, features from an image and/or image sequence that pertain to the microcirculation state of the tissue are extracted. For example, image analysis tools may be utilized to identify features by shape (e.g., various vessel sizes, vessel branching points) and/or temporal behavior (e.g., flow velocity, variability of flow rate). In various embodiments, processing steps may include de-noising, edge-preserving filtering, Fourier/bandpass filtering, convolution and modal de-composition, background subtraction, illumination flattening, removal of macroscopic movement artifacts, morphological operations, thresholding, or segmentation, among others.

At 130, a quantitative index of flow state is generated. Information extracted from flow images may be used to generate one or more quantitative parameters that represent one or more properties of the microcirculatory state of the tissue. Examples of observable quantities include the fraction of tissue area showing active blood flow, a number (or combined length) of perfused vessels of a certain size, distribution of perfused vessel sizes in the image, flow rate in vessels of specified size, or distribution of distances among neighboring vessels, as well as variation and trending of such quantities. In some embodiments, a combination of any of these (and/or other) quantities extracted from flow imaging may be used to construct one or more monitoring parameters that describe a local state of tissue microcirculation in a form useful for clinical detection and monitoring of events relevant to a specific patient condition such as sepsis. Further, additional classification steps may be applied to flow image maps, including classifications similar to conventional classifications used in video-microscopy data of microvasculature.

Figure 2:
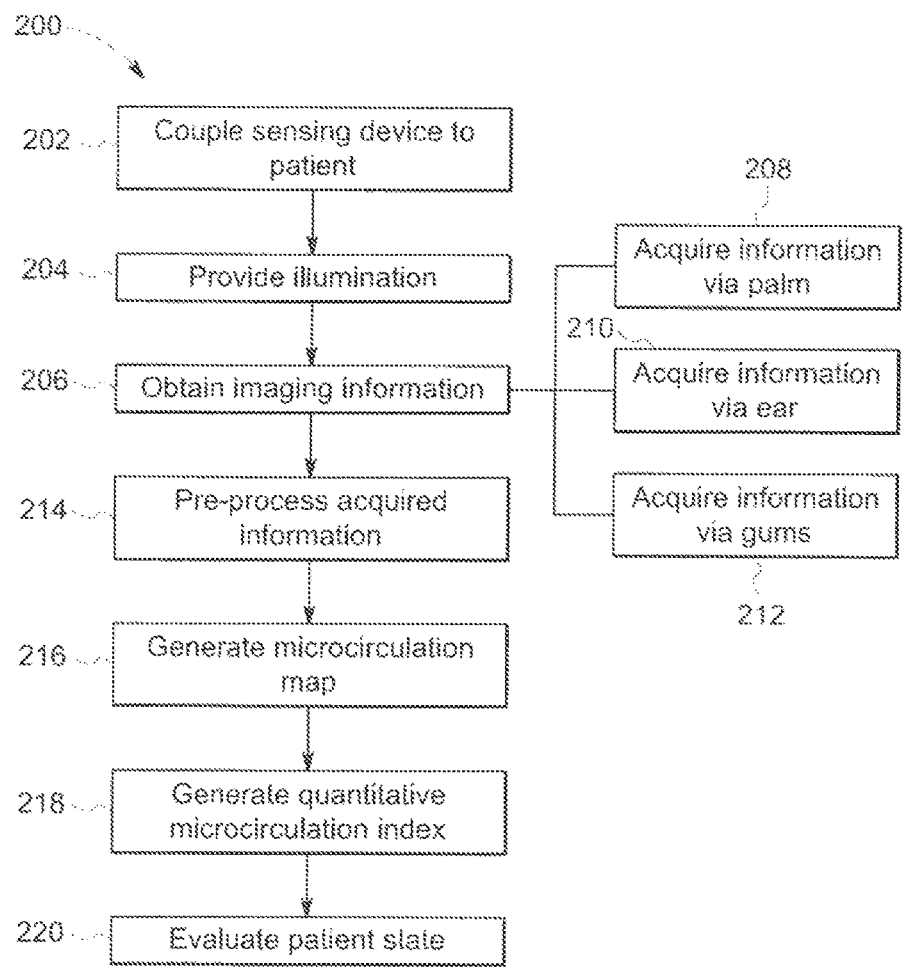
FIG. 2 is a flowchart of a method for monitoring a patient in accordance with various embodiments.

FIG. 2 provides a flowchart of a method 200 for monitoring a patient in accordance with various embodiments. In various embodiments, the method 200, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be able to be used as one or more algorithms to direct hardware to perform operations described herein.

At 202, a sensing device is coupled to a patient. Generally, the sensing device is configured to acquiring flow-sensitive imaging information from the patient using an illumination source and a detector. The illumination source, for example, may include a coherent source such as a laser, and the detector may include a camera such as a CMOS or CCD camera. The sensing device may be affixed, mounted, or otherwise coupled to the patient in a fixed or semi-fixed fashion such that an operator need not hold the sensing device in place. As one example, the sensing device may be provided with an earpiece and strap configured to be secured to a patient's head and to image tissue of the ear. As another example, the sensing device may be affixed to a patient's palm (e.g., using an adhesive pad) and configured to image tissue of the patient's palm. As one more example, the sensing device may be associated with a tube or other structure used in connection with ventilation and configured to image tissue of a patient's gums.

At 204, illumination is provided. The illumination is provided to the sensing device to facilitate image acquisition. The illumination source may provide coherent light such as a laser to be used in conjunction with laser speckle imaging to detect and image flow of blood through a FOV of the tissue. Optionally, an auxiliary illumination source may provide an incoherent light source to provide information used to process the information obtained via the coherent light source (e.g., to generate a model and/or to be used in conjunction with motion stabilization, de-noising, or averaging). Further, additional information obtained via the auxiliary illumination source may be utilized in determining one or more parameters used in determining a microvascular perfusion index (e.g., one or more parameters may be obtained using the coherent light source and one or more parameters may be obtained using the incoherent light source).

At 206, imaging information is acquired or obtained. In the depicted embodiment, the imaging information is obtained using a flow-sensitive optical technique, such as laser speckle imaging. The imaging information may be acquired in a series of images at a predetermined sample rate. The resolution of the imaging technique as well as the sampling rate may be configured to provide sufficient information for identification of flow through microvasculature as well as variations in flow through microvasculature. Imaging information may be acquired at one or more locations or regions of a patient, for example using one or more of sub-steps 208, 210, 212. In some embodiments, auxiliary imaging information may be obtained using an auxiliary light source, such as one or more LEDs.

At 208, imaging information is acquired from a palm of a patient, for example using a sensing device affixed to the palm via an adhesive pad. Additionally or alternatively, at 210, imaging information is acquired from an ear of the patient, for example using a headpiece or earpiece mounted to a patient. Acquiring information from a patient's ear may provide better resolution relative to the palm due to proximity of underlying blood vessels to the surface. As one more example, at 212, imaging information may be obtained from the gums or other region inside a patient's mouth. For example, a sensing device may be coupled to a ventilator attachment disposed within a patient's mouth. Generally, use of a sensing device mounted to a patient allows for continuous collection of information without requiring an operator to hold the device in place and/or provide a visual observation of tissue being analyzed. Thus, in contrast to conventional approaches such as observing vasculature periodically under a patient's tongue, various embodiments provide for continuous (instead of occasional or intermittent) monitoring, as well as for automatic (instead of manual) monitoring, thereby improving the consistency and reliability of monitoring, as well as reducing operator effort. In various embodiments, imaging information may be acquired continuously at a predetermined sampling rate over a collection period or monitoring period during which one or more sensing devices are operably coupled to a patient.

At 214, pre-processing is performed. The pre-processing may include de-noising, filtering, motion correction, or the like. In some embodiments, pre-processing may be performed using auxiliary imaging information acquired via an auxiliary illumination source. For example, information acquired using a non-coherent light source may be used to de-noise and/or motion correct flow information acquired via a coherent light source. Additionally or alternatively, auxiliary information acquired via a non-coherent light source may be used to generate additional parameters used to generate a quantitative microcirculation index or microvascular perfusion index.

At 216, a microcirculation map of microvasculature of the patient is generated using the imaging information acquired at 206 and/or pre-processed at 214. The microcirculation map may depict, describe, or correspond to the size, structure, and/or distribution of microvasculature (e.g., capillaries, venules connected to the capillaries, arterioles coupled to the capillaries) within a FOV of a detection device. In some embodiments, a sequence of maps may be generated at regular time intervals over a collection or monitoring period, allowing for not only determinations regarding microcirculatory state at a particular time, but also for variations or trends in microvascular characteristics over time.

At 218, a quantitative microcirculation index is generated based on the microcirculation map. The quantitative microcirculation index corresponds to a condition of the patient, such as sepsis. The particular parameters used, as well as the values of the parameters and/or index that are used to identify existence and/or onset of a particular condition may be configured to suit a particular application, and may be developed using historical information and/or information obtained via clinical studies. In various embodiments, one or more parameters may be determined based on one or more microcirculation maps and used to generate the quantitative microcirculation index. For example, a percentage of tissue with flow, a number and/or length of vessels within one or more size ranges, branching, or the like determined using one or more microcirculation maps may be used to provide one or more parameters that may be used to generate an objective microcirculation index. The index may be generated based on a static condition (e.g., using one map obtained at a given point in time) and/or may be generated based on dynamic conditions (e.g., trends or variations in microcirculation over time). The quantitative microcirculation index may be generated at least in part via a comparison of an acquired microcirculation map with a model map. The model map may be a map derived from an earlier or previous acquisition of a given patient (e.g., a baseline measurement collected at the beginning of a monitoring round), or be a map derived from a time window surrounding acquisition of a given map. In some embodiments, one or more parameters determined from imaging information acquired via an auxiliary illumination source (e.g., a non-coherent source) may be used in conjunction with information extracted from a microcirculation map to generate a quantitative microcirculation index. For example, positions of some of the vessels within FOV may be determined from a non-coherent image information such as local absorption of diffused light, while the presence of absence of flow may be assessed from the flow map produced by coherent imaging.

In some embodiments, the quantitative microcirculation index (e.g., a parameter used to generate the quantitative microcirculation index) corresponds to a percentage of vessels that satisfy at least one threshold. For example, a percentage of identified vessels that do not exceed 20 micrometers may be used as a parameter. In some embodiments, more than one vessel size threshold may be employed. For example, a percentage of identified vessels that do not exceed 20 micrometers may be used as a first parameter, and percentage of identified vessels that exceed 20 micrometers and are below 50 micrometer may be used as a second parameter. The percentage may additionally or alternatively be stated in terms of total area of a FOV. For example, a percentage of the area of a FOV occupied by vessels having a diameter exceeding a given value may be used as a parameter.

Additionally or alternatively, in some embodiments, the quantitative microcirculation index (e.g., a parameter used to generate the quantitative microcirculation index) corresponds to at least one of an amount of change or a rate of change of a vessel size parameter, such as number, total length, distribution, or proportion of vessels falling within one or more size ranges. Thus, changes in microcirculation over time may be utilized to generate one or more parameters used to generate a microcirculation index. Further additionally or alternatively, in some embodiments, the quantitative microcirculation index (e.g., a parameter used to generate the quantitative microcirculation index) corresponds to a ratio of a first group of vessels within a first size range to a second group of vessels within a second size range. For example, a ratio (e.g., in terms of number of vessels, or in terms of total length of vessels) under 20 micrometers to vessels between 20 micrometers and 50 micrometers may be used as a parameter to generate a quantitative microcirculation index.

At 220, a condition or state of the patient is evaluated using the quantitative microcirculation index. For example, in some embodiments, if the index exceeds a threshold value, and/or varies above a threshold rate, it may be determined that a condition affecting microcirculation (e.g., sepsis) has begun. Remedial action may be taken responsive to the determination. For example, a warning, alert, or other message may be provided to a practitioner indicating the onset of the relevant condition. Multiple indices corresponding to multiple conditions may be monitored. Further, after a remedial action such as administration of fluids and/or medication has commenced, continued monitoring of the index (or indices) may be employed to track the progress of the condition. For example, if the condition is determined to be worsening, a message may be provided to a practitioner indicating that a previously taken remedial action has not been sufficiently effective. As another example, if the condition is determined to be improving, a message may be provided to a practitioner indicating the course of action is being effective and may be reduced, if appropriate. Further, the quantitative microcirculation index may be combined with other known vital sign signals in a clinical decision support system that uses multi-parameter algorithms to assess likelihood of various patient states and trends and provide recommendation to the care provider. Thus, various embodiments assist in the diagnosis of medical conditions, and the monitoring of progression and response to treatment of medical conditions that impact microvascular flow.

Figure 3:
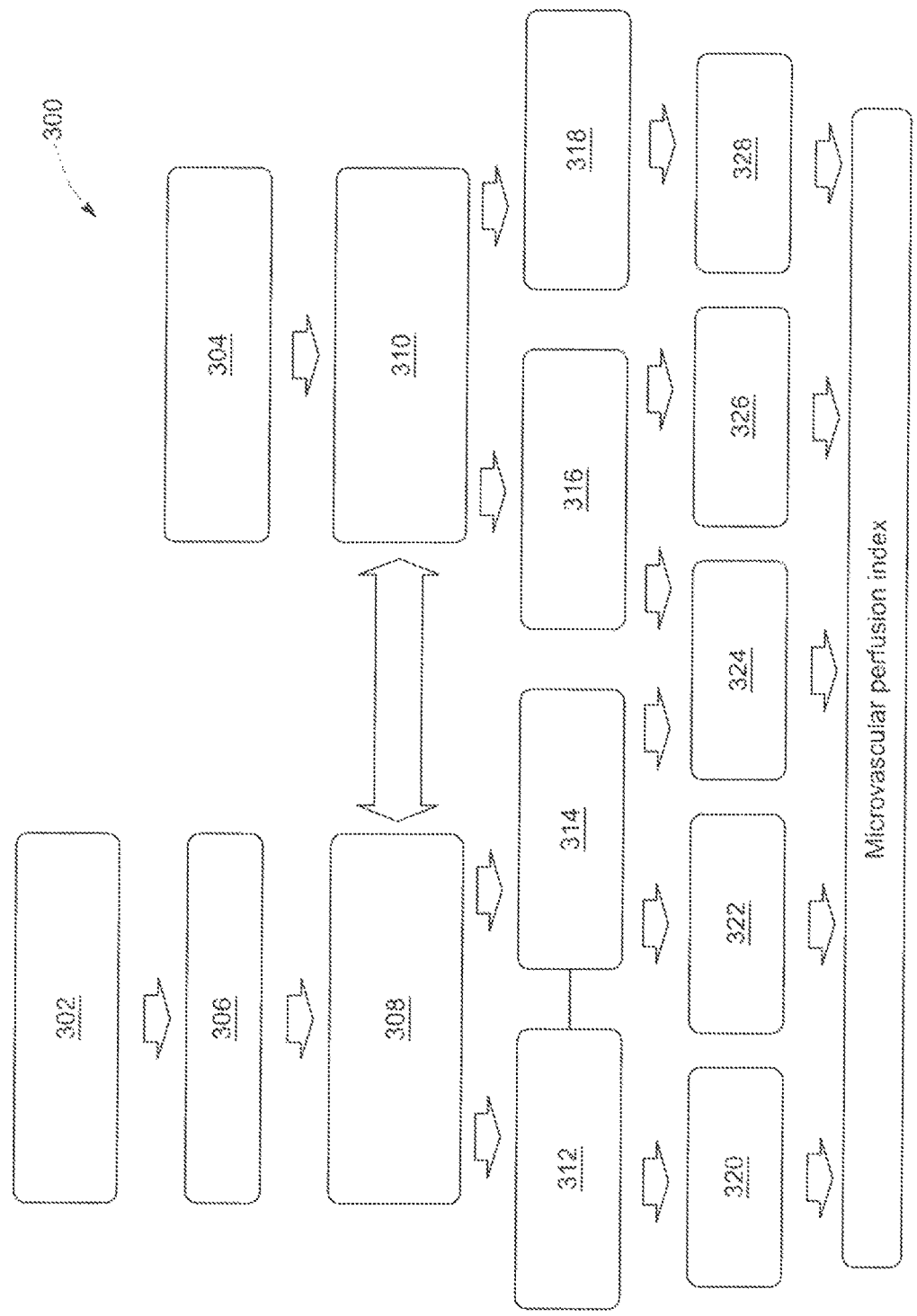
FIG. 3 is a flowchart of a method for generating a microvascular perfusion index or quantitative microcirculation index using laser speckle imaging and auxiliary imaging in accordance with various embodiments.

As indicated herein, auxiliary imaging information (e.g., information obtained via an incoherent light source) may be used in conjunction with flow-sensitive imaging information (e.g., information obtained via a coherent light source). FIG. 3 provides a flowchart of a method 300 for generating a microvascular perfusion index or quantitative microcirculation index using laser speckle imaging and auxiliary imaging in accordance with various embodiments. In various embodiments, the method 300, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be able to be used as one or more algorithms to direct hardware to perform operations described herein.

At 302, laser speckle imaging information is acquired. The information may be acquired at a resolution and sampling rate sufficient to allow for the identification of microvasculature as well as variations in microvasculature due to circulation. In the illustrated embodiment, the laser speckle imaging information is acquired using a laser at a red or near-infrared wavelength between 600-1000 nanometers (e.g., 970 nanometers) and at a high-speed acquisition rate of between 50-200 camera frames per second (e.g., 150 frames or images per second).

At 304, auxiliary information is acquired. In the illustrated embodiment, the auxiliary information is acquired at a visible wavelength (e.g., 520-550 nanometers) and at a low-speed acquisition rate (e.g., 8 frames or images per second). In various embodiments, the auxiliary information may be acquired intermittently at larger time intervals.

After acquisition of laser speckle imaging information and auxiliary information, the acquired information may be processed. For example, at 310, spatial contrast processing may be performed on acquired auxiliary imaging information. Spatial contrast processing may include one or more of re-focusing, image registration, or alignment. In some embodiments, visual markers that are transparent to infrared wavelength may be placed on the region of interest to guide the auxiliary image registration if there is not enough textural information.

At 306, temporal contrast processing is performed on the acquired laser speckle imaging information. In some embodiments, a coefficient of variation calculation may be applied to a stack of 25 raw speckle images (or a series of about 25 consecutive raw speckle images) to provide a sequence of contrast images at a reduced frame rate (relative to the original acquisition rate). At 308, the sequence of contrast images may be averaged to reduce noise. Further, motion compensation and other de-noising filtering techniques may be applied at 308 to improve vessel visualization contrast. Further still, motion compensation may be further expanded to motion correct the stack or sequence of raw images to further improve the speckle image quality. It may be noted that certain aspects of de-noising and/or motion compensation may utilize information obtained via auxiliary imaging at 304 and/or processed at 310.

In the next level of steps, information may be processed to provide one or more circulation maps or other representations used to generate parameters for use in generating a quantitative microcirculation index or microvascular perfusion index. For example, at 314 a topological analysis (e.g., multi-scale Frangi algorithm) may be performed and at 312 an intensity analysis (e.g., vessel density algorithm) may be performed on laser speckle information (e.g., pre-processed laser speckle information). For example, the images resulting from step 308 may be subject to a multi-scale vessel enhancement filter, for example based on a Frangi algorithm. Such an algorithm may be effective on laser speckle images for vascular network with sizes including 20 micrometers or below. The application of the Frangi algorithm may produce a probability map of finding a vessel of a specific diameter at a location across the image. Based on the probability map, binning of pixels corresponding to different vessel sizes may be performed, and the relative fractions of the field of view may be plotted as function of time. A skeleton transform is another example of a technique that may be employed to define a morphological skeleton of a vessel image to be used in quantification of a field of view by vessel width and/or length. A skeleton transform may define shapes of vessels by evaluating a distance to the nearest background point for each pixel in an image.

Processed information from auxiliary information from 310 may also be further processed. For example, at 316, a morphological analysis may be performed on auxiliary information, for example by analyzing vessel contours via differential contrast. As another example, at 318, more than two auxiliary images may be acquired using different wavelengths of auxiliary incoherent light source and processed to obtain spectroscopic information on the visualized vasculature.

At the next level of steps, one or more microcirculation maps and/or other results of image acquisition and analysis may be used to generate one or more parameters used to determine a quantitative microcirculation index. For example, at 320, vessel flow density may be analyzed (e.g., via flow tracking), and at 322 vessel length may be analyzed (e.g., via a multi-scale segmentation). At 324 of the illustrated embodiment, vessel thickness is analyzed using a skeleton transform. Additionally, at 326, vessel branching is analyzed, for example using a T-junction transform. Further, in the illustrated embodiment, at 328, vessel oxygenation is analyzed, for example using $HbO_2$ mapping of auxiliary information.

Accordingly, both laser speckle and auxiliary information may be utilized to generate one or more indices representative of microvascular flow and/or representative of a condition or onset of a condition of a patient (e.g., sepsis). It may be noted that various embodiments as described herein may further be used as part of a monitoring system including other types of monitors such as pulse oximetry, capnography, heart rate monitoring, respiratory monitoring, blood pressure monitoring, or the like.

Figure 4:
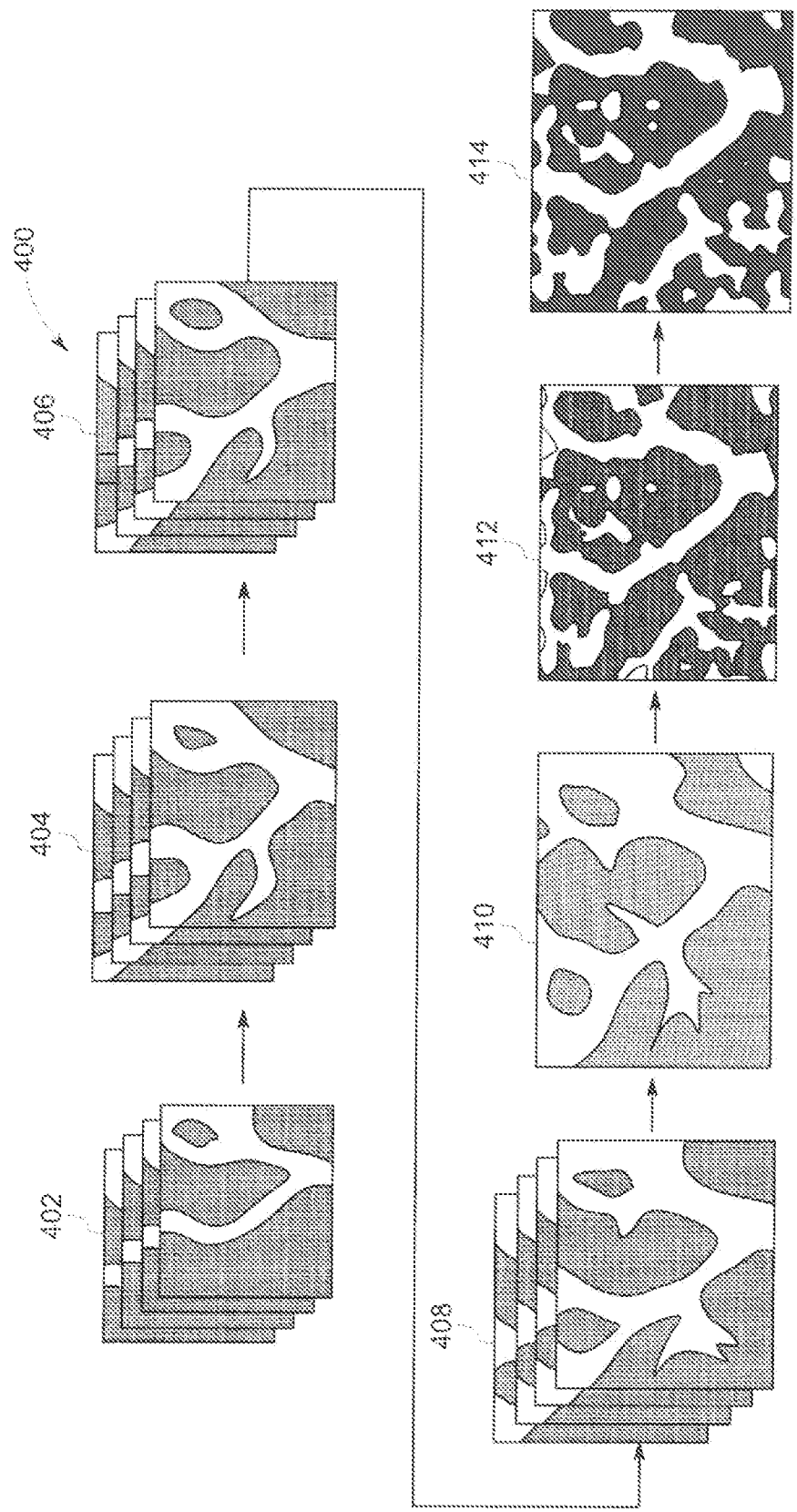
FIG. 4 provides a flowchart of a method for generating a microvascular perfusion index or quantitative microcirculation index using laser speckle imaging and auxiliary imaging in accordance with various embodiments.

In some embodiments, a workflow may consist of two phases, namely a first phase in which acquired raw speckle images are enhanced and used to estimate a probabilistic vessel model from a time series (e.g., a time series acquired during non-occlusion or an amount of perfusion associated with the baseline circulation), and a second phase in which a perfusion index is quantified using the probabilistic vessel model estimated previously. FIG. 4 provides a flowchart of a method 400 for generating a microvascular perfusion index or quantitative microcirculation index using laser speckle imaging and auxiliary imaging in accordance with various embodiments. In various embodiments, the method 400, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware to perform operations described herein.

At 402, raw contrast data is acquired (e.g., using laser speckle imaging). For example, raw contrast data may be acquired to provide a temporal sequence of images corresponding to perfusion, which may be input to the remaining aspects of method 400. At 404, 3D (2D+time) preprocessing is performed to provide a sequence of images as depicted. For example, the temporal sequence of images from 402 may be 3D filtered using an anisotropic median filter in the input sequence to enhance the signal to background noise ratio. At 406, motion compensation may be performed. For example, a motion-compensation algorithm may be applied by registering the image sequence. All the images may be mapped to the same image coordinate system to help ensure that pixels corresponding to different sections of the vessels match from image to image in the sequence. At 408, 3D post-processing may be performed. For example, with the image sequence aligned temporally, a post-processing step may be applied to enhance the overall vasculature.

Specifically, for example, in some embodiments, post-processing may be performed on short frame sequences sampled periodically along the duration of information acquisition. These image sequences may be averaged over 10-50 frames to increase signal to noise ratio and to provide a time-averaged image of perfusion. The averaged images may be further aligned and registered either automatically or manually, and the individual vessels may be traced.

In one embodiment, the averaged images may be scaled linearly using a relationship of $I_{out}=(I_{in}-_{min})$, and stored as 8-bit AVI files. A median filter with a radius of 1-100 pixels may be applied to each resultant frame. A Hessian-based filter (such as Frangi) may be applied to the frames after the median filtering. In this embodiment, parameters of the filter may be selected such as to capture vessel features that are anywhere between 10 and 50 um in diameter. In particular, a range of sigma values: 3, 5, 7, 9, 11 corresponding to FWHM of 12, 20, 28, 36, 44 µm in LSI images was found to be practical. The filter produces smoothed images, as well as a histogram of image pixels corresponding to vessels of different diameter. This histogram may be used to single out the predominance of a subset of vessels reproduced by the filter. Individual vessels may be traced.

Following vessel tracing, the following microvascular parameters may be computed, for example:

Linear density of small (≤20 µm) vessels [in $mm/mm^2$];
Linear density of other (>20 µm) vessels [in $mm/mm^2$];
Vessel density in the field of view [in #/mm];
Total length of identified vessels in the field of view [in #/mm].

In some embodiments, adding symmetric (mirror) boundary conditions to Gaussian 2nd derivatives in Hessian computation may be utilized to improve image quality by removing edge shadowing and artifacts.

In various embodiments, image inversion may be utilized to help a Hessian-based filter algorithm capture features corresponding to the smallest vessels.

In the depicted embodiment, it is assumed that there is a high correlation of the pixels corresponding to the vessel over time, enabling suppression of noise in the background. At 410, a reference mean image is estimated. For example, in the illustrated embodiment, as seen in the image depicted at 410, a 2 dimensional projection of the enhanced vasculature is projected along a temporal axis. For example, a simple averaging may be performed to project the sequence. At 412, vessels are detected. In the illustrated embodiment, the projection from 410 is used to compute a probability map of the vessel depicted at 412 by applying eigenvalue analysis derived of the Hessian matrix at multiple scales. Vessel segmentation is performed at 414. For example, a threshold operation may be applied to every pixel above a given probability using the results of 412. A vessel model as discussed in relation to FIG. 4 may be developed at an initial time corresponding to the baseline perfusion, and/or may be developed at regular intervals during a monitoring period in various embodiments. It should be noted that several vessel segmentation maps may be produced representing locations of vessels with different dimensions (e.g., diameter within different range of values).

Figure 5:
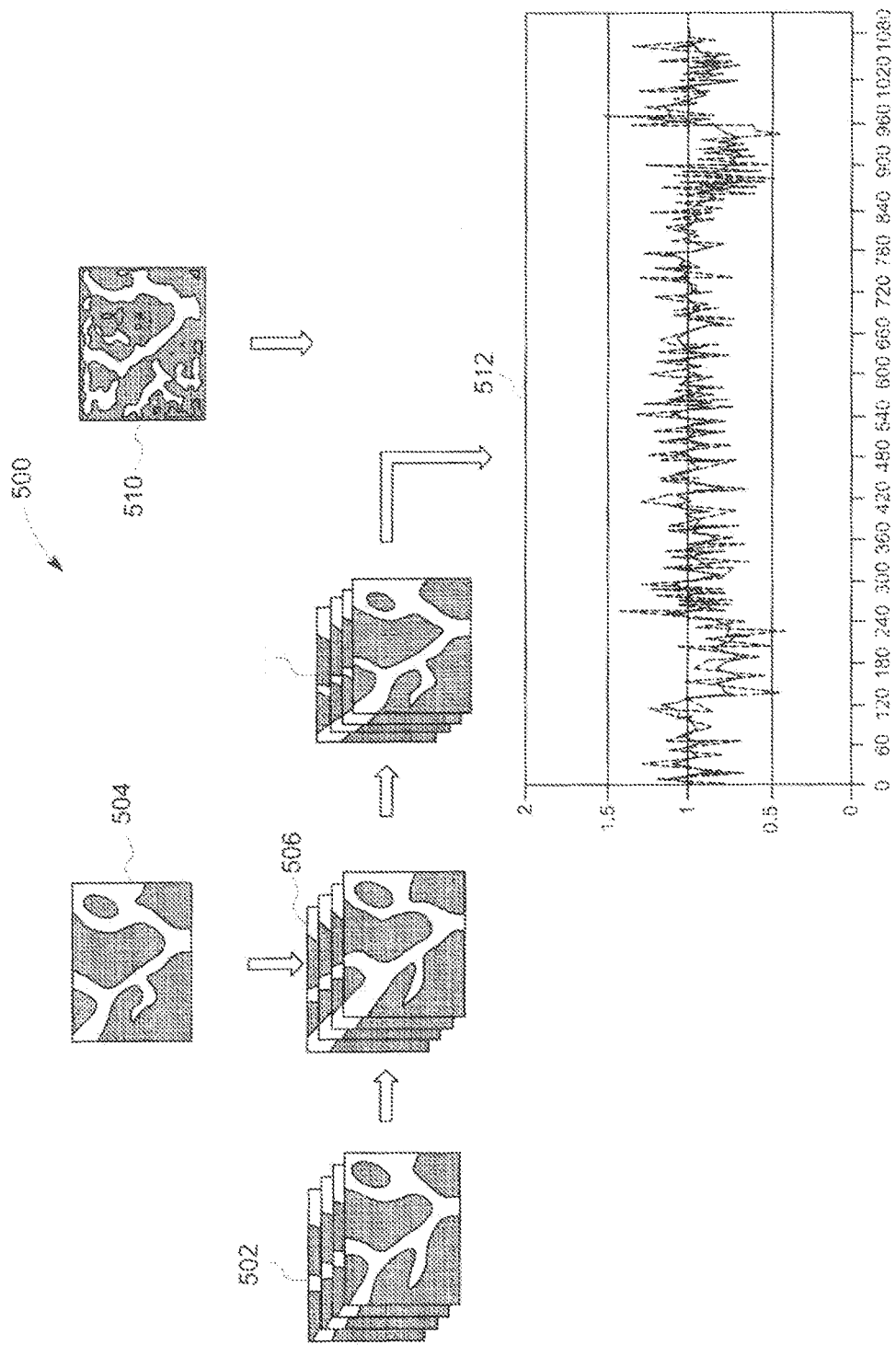
FIG. 5 provides a flowchart of a method for generating a microvascular perfusion index or quantitative microcirculation index using a model.

FIG. 5 provides a flowchart of a method 500 for generating a microvascular perfusion index or quantitative microcirculation index using a model (e.g., a model developed using method 400). Generally, an estimated mean reference image (e.g., as developed at 410) and an estimated vessel model (e.g., as developed at 412) may be used to compensate frame-to-frame motion in a new sequence of data, and to quantify flow rates in real time, respectively. In some embodiments, first, the mean reference image may be used to compensate for motion, providing a high signal to noise ratio (SNR) reference image for aligning the time sequence, followed by an image post-processing step to enhance the SNR. Next, the vessel segmentation model may be used to quantify perfusion the vessel area. For example, one flow rate metric that may be used is densities of vessels of different sizes as described in method 300.

In various embodiments, the method 500, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware to perform operations described herein.

At 502, a time series of raw images is acquired, for example, using laser speckle imaging or other imaging modality for which flow through microvasculature may be observed or detected at a sufficient resolution. At 504, a reference mean image is generated, for example as discussed above in connection with FIG. 4. At 506, motion compensation is performed on the time series of raw images from 502 using the reference mean image from 504. The resulting motion compensated information is then post-processed at 508, for example to enhance the overall vasculature and/or an image quality metric such as SNR. At 510, a reference vessel map is developed, for example as discussed above in connection with FIG. 4. At 512, the resulting information from the post-processing at 508 and the reference vessel map are used to generate a quantitative microcirculation index. For example, one or more values determined from the results of the post-processing at 508 (e.g., pixel intensities) may be analyzed using the reference vessel map as a guide. For instance, a comparison of pixel intensities between expected vessel pixels and expected background pixels may be analyzed to provide an objective measure of flow through vessels in the FOV. Several segmented vessel maps may be produced to identify locations of vessels of various sizes. These maps may be used to generate the corresponding numerical values representing the predominance of flow in these vessel sizes. Subsequently, these values may be combined into a quantitative microcirculation index, for example as a ratio of flow in vessels of different sizes as described in connection with method 200. In FIG. 5, the index is depicted over time, allowing for trends or variations in the index to be observed. It may be noted that a number of different parameters (and/or a variation of one or more parameters and/or or rate of change of one or more parameters) may be used to provide the index.

As discussed herein, the use of a first imaging modality (e.g., laser speckle imaging) to produce an image of a vascular map of microvasculature may be complemented or supplemented with one or more additional imaging modalities. For example, diffused reflection imaging may be implemented in some embodiments using wavelengths of light that exhibit absorption by blood (e.g., by hemoglobin in red blood cells). For instance, light in the green region of the visible spectrum (e.g., about 532 nanometers) is strongly absorbed by hemoglobin). Light may penetrate tissue, undergo scattering in the tissue, and eventually escape in a backward direction, generally similar to the passage of light from a laser through tissue. However, in connection with diffused reflection imaging or other absorption contrast technique, green light passing through vessels filled with blood will be partially absorbed, creating a contrast image from a sensor. With appropriate selection or configuration of the light source and detection parameters, an image map of vessels may be produced. It may be noted that, in contrast to a map generated using laser speckle information, an image using absorption contrast information will represent the presence of blood in vessels or vessels containing blood, and not a flow map.

In various embodiments, absorption contrast and laser speckle images may be acquired intermittently from a common tissue region of interest (e.g., via synchronized modulated illumination) and used as complimentary data. For example, an absorption-based image may serve as reference for localization of vessel positions and optimization of focusing. An absorption-based image may be superimposed onto laser speckle information to extract flow velocity or related quantities with better specificity. Additionally, absorption contrast may be used to help differentiate between arterial and venous flow across an image. For example, information distinguishing between arterial and venous perfusion may provide one or more additional quantifiable parameters that correlate with the onset and/or progression of the disease state.

In some embodiments, due to the pulsatile character of blood flow, an external signal characteristic of timing of the heart beat (e.g., ECG or photoplethysmograph waveforms) may be advantageously employed to synchronize acquisition of flow image data with one or more aspects of a cardiac cycle. For example, in various embodiments, flow images may be time-stamped or otherwise identified with respect to systolic phase of the heart cycle, and subsequent image processing and/or index or parameter extraction may be performed in a phase-locked fashion. For example, all frames with a similar timing within the cardiac cycle may be processed together. Additionally or alternatively, image acquisition may be triggered by an external signal synchronized with a cardiac cycle. In some embodiments, variability of flow over the cardiac cycle may be analyzed to extract parameters related to localized vessel compliance in response to pressure changes.

Figure 6:
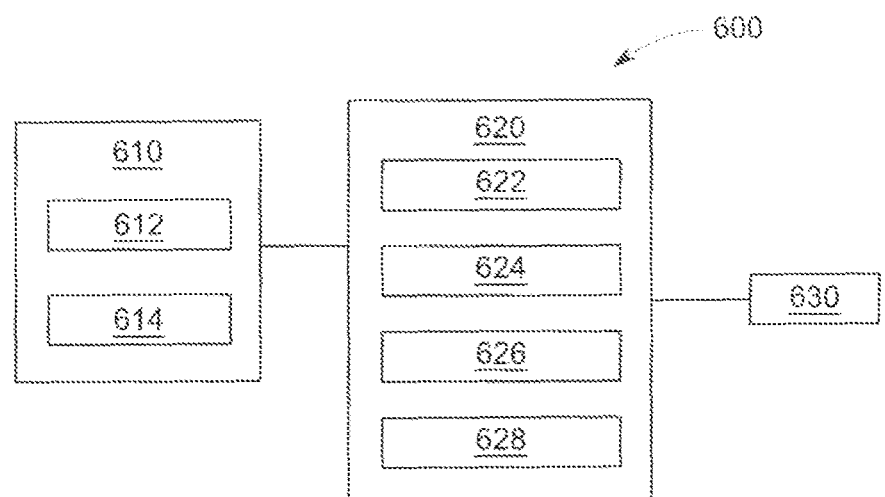
FIG. 6 is a schematic block diagram of a detection system formed in accordance with various embodiments.

FIG. 6 is a schematic block diagram of a detection system 600 formed in accordance with various embodiments. The detection system 600, for example, may be configured to perform or be used in connection with one or more of the methods or process flows discussed herein. The detection system 600 may be configured to acquire flow information corresponding to microvasculature and to generate a value (or values) for one or more quantitative microcirculation indices that may be used in connection with diagnosing a patient, for example identifying onset of sepsis and/or tracking the progress of a treatment for sepsis. The detection system includes a detection unit 610, a processing unit 620, and a display 630. Generally, the detection unit 610 is configured to acquire microcirculation information (e.g., information corresponding to or describing the flow of blood through microvasculature), and the processing unit 620 is configured to process and analyze the acquired information to generate one or more quantitative microcirculation indices. It may be noted that various embodiments may include additional components, or may not include all of the components shown in FIG. 6 (for example, various embodiments may provide sub-systems for use with other sub-systems to provide an imaging system). Further, it may be noted that certain aspects of the detection system 600 shown as separate blocks in FIG. 6 may be incorporated into a single physical entity, and/or aspects shown as a single block in FIG. 6 may be shared or divided among two or more physical entities.

The depicted detection unit 610 includes an illumination unit 612 and a collection unit 614. Generally the illumination unit 612 includes one or more sources of light or illumination that are directed toward a tissue region of interest to be analyzed, and the collection unit 614 collects or acquires optical information from the illuminated tissue region of interest. The illumination unit 612 may be operably coupled to the processing unit 620, which may control the operation of the illumination unit 612. Similarly, the collection unit 614 may be operably coupled to the processing unit 620, which may control the operation of the collection unit 614 and/or obtain imaging information from the collection unit 614. All or a portion of the detection unit 610 may be configured for mounting or affixing to a patient. For example, in embodiments where the tissue region of interest is a portion of an ear, at least a portion of the detection unit 610 may be incorporated into an ear piece secured to a patient head using a strap or other mounting device.

The illumination unit 612, for example, may include a laser configured to provide illumination for laser speckle imaging. Laser speckle imaging is an imaging technique that may be employed to assess motion in scattering media. Generally, laser speckle imaging relies on detection and processing of intensity speckle patterns that result from interference effects of a coherent laser light scattered off an object (e.g., biological tissue). The movement of blood cells in tissue results in redistribution of the optical propagation path and temporal and spatial variation of the speckle patterns, which may be processed to reconstruct a surface map of blood flow distribution. Biological tissues exhibit higher transparency in the red and near infrared wavelength range of the spectrum. Various embodiments may utilize red and/or near infrared wavelengths for laser speckle imaging to probe or detect blood flow disposed beneath a surface of tissue. It may be noted that the illumination unit 612 may include more than one light source. For example, the illumination unit 612 may include a coherent light source (e.g., laser) and an incoherent light source (e.g., light emitting diode (LED)).

The collection unit 614 includes one or more optical detection devices, such as a CMOS camera or CCD camera. Generally, the collection unit 614 is configured to acquire optical image information corresponding to microcirculation of a patient. The information collected by the collection unit 614 may be acquired by the processing unit 620, and used to determine a value for one more quantitative microcirculation indices as described herein. It may be noted that the detection unit 610 may include additional components, for example, as discussed in connection with FIGS. 7-10.

As discussed herein, laser speckle imaging (LSI) may be used in connection with acquiring flow-sensitive imaging information in various embodiments. Alternatively or additionally, other flow-sensitive imaging techniques may be employed in various embodiments. For example, in some embodiments, ultra-sonic images, optical coherence tomography (OCT), laser Doppler imaging (LDI), or photoacoustic imaging may be utilized. It may be noted that the ultrasonic modality may be used to image structure of the biological tissues, including the blood flow in vasculature; however, imaging of vessel sizes typical to microvascular networks may require use of ultrasound contrast enhancing agents. It may be noted, for example, the OCT is capable of providing true 3D structural images of tissue with about 10 micrometer resolution as well as blood flow; however, OCT may require a coherent broad band source that may substantially add to the cost of a system. Accordingly, use of laser speckle imaging may be more cost-effective than OCT. It may also be noted that LDI is based on raster scanning (which may limit LDI in terms of resolution-speed trade off in comparison to laser speckle imaging) or relies on the use of high-speed imaging devices, which may add to system cost. Accordingly, laser speckle imaging in various embodiments may provide cost and/or resolution benefits in comparison to other potential imaging techniques.

As indicated herein, the processing unit 620 is configured to control various aspects of the detection unit 610 (e.g., focusing, timing of illumination, or timing of acquisition, among others) and/or to process information acquired via the detection unit 610 to quantify microcirculation of a patient. The processing unit 620 of the illustrated embodiment is configured to perform one or more aspects discussed in connection with the methods or process flows disclosed herein.

The depicted processing unit 620 is operably coupled to the detection unit 610. The processing unit 620, for example, may receive imaging data from the detection unit 610. As another example, the processing unit 620 may provide control signals to the detection unit 610, for example, to adjust a focus, or as another example, to selectably control operation of light sources (e.g., to alternate operation of a coherent light source with operation of an incoherent light source). The processing unit 620 may include processing circuitry configured to perform one or more tasks, functions, or steps discussed herein. It may be noted that "processing unit" as used herein is not intended to necessarily be limited to a single processor or computer. For example, the processing unit 620 may include multiple processors and/or computers, which may be integrated in a common housing or unit, or which may distributed among various units or housings. It may be noted that operations performed by the processing unit 620 (e.g., operations corresponding to process flows or methods discussed herein, or aspects thereof) may be sufficiently complex that the operations may not be performed by a human being within a reasonable time period. For example, the processing of imaging data and/or automatic control of a detection unit as discussed herein may rely on or utilize computations that may not be completed by a person within a reasonable time period.

In the illustrated embodiment, the processing unit 620 includes a map generation module 622, an index module 624, a diagnostic module 626, and a memory 628. It may be noted that other types, numbers, or combinations of modules may be employed in alternate embodiments, and/or various aspects of modules described herein may be utilized in connection with different modules additionally or alternatively. Generally, the various aspects of the processing unit 620 act individually or cooperatively with other aspects to perform one or more aspects of the methods, steps, or processes discussed herein.

The depicted map generation module 622 is configured to acquire imaging information from the detection unit 610 and to generate one or more microcirculation maps corresponding to flow of blood through microvasculature. For example, the map generation module 622 may receive a frame of information or a series of frames of information from the detection unit 610, determine flow through microvasculature based on speckle patterns, and generate one or more maps representative of the flow of blood (e.g., vessels through which the blood flows) based on the speckle patterns.

The index module 624 depicted in FIG. 6 is configured to generate a quantitative microcirculation index based on the microcirculation map generated by the map generation module 622. For example, the index module 624 may identify and extract features corresponding to vessels size (e.g., vessel width, length, proportion of perfused area to non-perfused area, ratio of total length of a first size range of vessels to total length of a second size range of vessels, or the like), and derive one or more parameter values based on the features. The index module 624 may then use a predetermined relationship (e.g., mathematical relation, look-up table) to generate a value for a microcirculation index based on the determined values of the flow parameter(s) and/or rate of change of values of flow parameter(s). The particular relationship between flow parameter(s) and microcirculation index value may be determined, for example, using historical information and/or clinical studies. In some embodiments, the index may be stated as a normalized value with respect to an initial or baseline value corresponding to non-occluded flow.

The depicted diagnostic module 626 is configured to determine a state or condition of a patient based on the quantitative microcirculation index. For example, when the index (or a rate of change thereof) satisfies a predetermined threshold, the diagnostic module 626 may determine an onset of sepsis, and provide a warning or alert to an operator. As another example, after onset of sepsis, the diagnostic module 626 may monitor the index value on an ongoing basis, and determine whether the condition is worsening or improving. Additionally or alternatively, the diagnostic module 626 may analyze one or more additional quantitative microcirculation indices and determine the presence, absence, or progress of conditions other than sepsis that are correlated with microcirculation.

The memory 628 may include one or more computer readable storage media. The memory 628, for example, may store acquired imaging information, values of parameters to be used in determining a microcirculation index, or the like. Further, the process flows and/or flowcharts discussed herein (or aspects thereof) may represent one or more sets of instructions that are stored in the memory 628 for direction operations of the system 600.

The display 630 is configured to provide information to the user. The display 630 may be configured to display, for example, a value of one or more determined parameters, one or more microcirculation maps, or a value of one or more quantitative microcirculation indices. The display 630 may additionally or alternatively be configured to provide an alert, warning, or message to an operator indicating that the values are consistent with onset of a condition (e.g., sepsis), and/or messages or prompts relating to the progress of a condition (e.g., messages indicating whether the condition is improving or worsening). The display 630 may be part of a multi-modality monitoring system and also display information from heart rate monitors or other patient monitoring devices. The display 630 may include one or more of a screen, a touchscreen, a printer, or the like.

Figure 7:
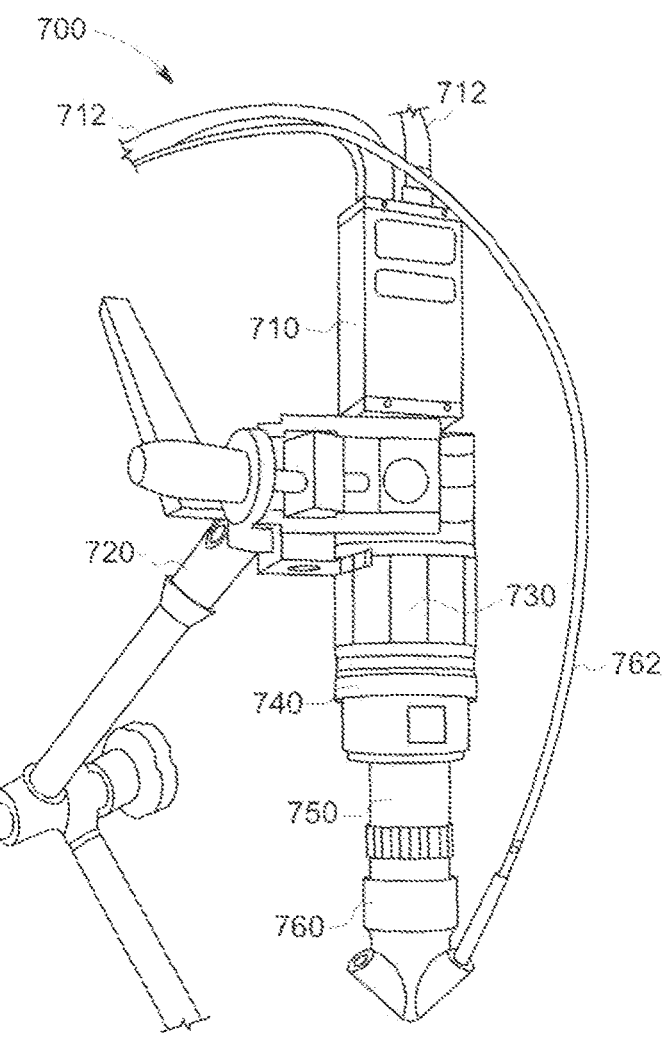
FIG. 7 is a schematic diagram of a detection system formed in accordance with various embodiments.

FIG. 7 illustrates an example detection system 700 formed in accordance with various embodiments. It may be noted that the example of FIG. 7 provides an example of data collection that may be used in a laboratory, and not necessarily as an embodiment for use with a patient in a clinical setting. The detection system 700 may be configured, for example, for use as a bench-top setup for use in a laboratory. The size of the system 700 or components thereof is not necessarily representative of embodiments configured for use in a clinic, and may be reduced for embodiments used in clinical settings. The depicted detection system 700 includes a camera 710, a positioning arm 720, a focusing unit 730, a polarizer 740, a microscope objective 750, and an illumination fixture 760. The camera 710 may be operably coupled to a processing unit (e.g., processing unit 620) via cables 712, and the illumination fixture 760 may receive light energy via fiber optic cable 762. For example, the illumination fixture 760 may receive light from a laser. The laser may be, for example, a single-mode 975 nanometer diode laser coupled to the illumination fixture 760 via fiber optic cable 762. In some embodiments, the laser source may be incorporated directly into the same unit as the optical detection system. The wavelengths between 600 and 1000 nm may be used as the light source in the flow-sensitive laser speckle imager. The camera 710, for example, may be a CCD camera capable of acquisition of 200 frames per second. In various embodiments, the sensor may be a CCD or a CMOS camera with frame rates from 30 to 200 frames per second or higher. The polarizer 740 may be interposed along a collection path between the camera 710 and the tissue being studied, with a transmission direction perpendicular to the polarization of the incident light, and may be used to reduce contribution from surface reflection relative to the contribution from diffused scattered light from inside the tissue. The various components may be configured to provide sufficient resolution for analyzing flow through microvasculature. Generally, in laser speckle imaging, useful resolution is limited by a combination of the optical resolution, speckle size, and camera pixel size. Optical resolution and speckle size may be determined by the wavelength and the optical system numerical aperture (NA), and may be related to cameral pixel size through a magnification parameter. To achieve an acceptable resolution range, the NA of the optical system in some embodiments may be between 0.2 and 0.4, and magnification between 1 and 5. In the present example, the following values may be utilized for parameters for the system 700:

| Parameter | Value |
| --- | --- |
| Magnification | 3.7 |
| NA | 0.28 |
| Optical resolution (object) | 2 micrometers |
| Wavelength | 975 nanometers |
| Speckle size (object) | 5 micrometers |
| Pixel size | 7.6 × 7.6 micrometers |
| Field of view | 1.3 × 0.96 millimeters |

The degree of flow at each pixel location may be characterized by a coefficient of variation (CV) of laser light intensity at a given location which may be calculated as $CV=\sigma/<I>$, where a is the standard deviation and $<I>$ is the mean value of the pixel intensity. The CV may be calculated over a spatial area of an image, or across a stack or sequence of images in a time sequence, or a combination of an image and a stack of images. Locations with underlying blood vessels perfused with blood exhibit movement of corresponding speckle patterns, and therefore a reduced speckle contrast when integrated over finite image acquisition time, while in areas of slower or no blood flow the speckle pattern is more static and the contrast is higher, providing the flow contrast of laser speckle imaging of blood flow through tissue.

Figure 8:
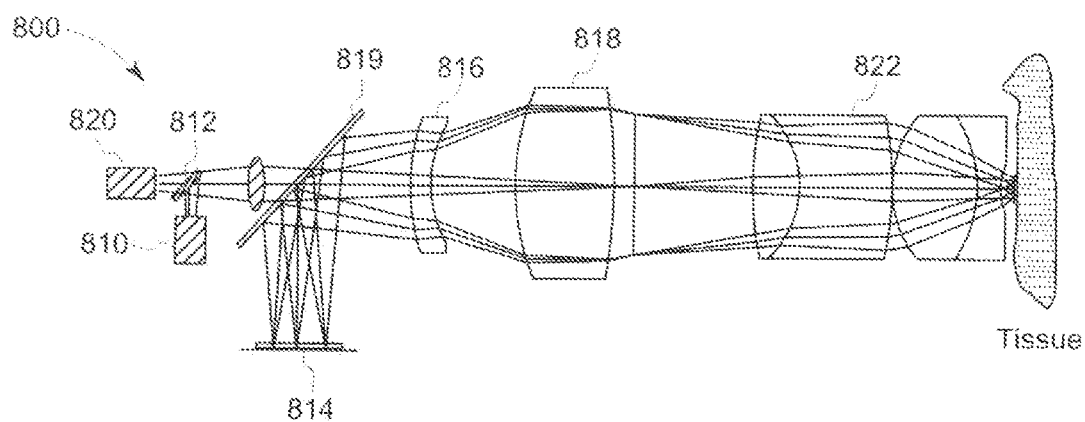
FIG. 8 is a schematic diagram of a detection system formed in accordance with various embodiments.

FIG. 8 illustrates a detection system 800 formed in accordance with various embodiments. It may be noted that the example discussed in connection with FIG. 8 is provided for illustrative purpose, and does not necessarily include all components that may be used in various embodiments. Other arrangements with additional and/or different components may be employed in various embodiments. The detection system 800 may be configured, for example, for use in a clinical setting (e.g., for mounting or affixing to a patient). The detection system 800 may have reduced size components relative to the system 700 for use with patients. The detection system 800 may be configured to provide a resolution of 5 micrometers or better in some embodiments, and may have a FOV of 2 millimeters×2 millimeters or large in some embodiments.

As seen in FIG. 8, the depicted detection system 800 includes an incoherent light source 810, a mirror 812 (e.g., dichroic mirror), a collection unit 814, a lens 816, an optical unit 818, a polarizing beam splitter 819, a laser diode 820, and an objective unit 822 including a spacer fixture. Generally, the various components depicted in FIG. 8 may have a size not exceeding 0.5 inches in any dimension, along with miniaturized optics tailored for a given application, to achieve a small footprint for convenient use while mounted to a patient over a continuous collection or monitoring period. It may be noted that the system 800 includes both coherent and non-coherent light sources, and may provide both microvascular flow imaging (e.g., using laser diode 820) as well as oxygenation mapping (e.g., using non-coherent light source 810). For example, the laser diode 820 and incoherent light source 810 may be activated in an alternating fashion, allowing for collection of both laser speckle information and auxiliary information as described herein over a common collection period. The incoherent light source 810, for example, may be a light emitting diode (LED) emitting green light or light having a wavelength of about 532 nanometers.

Light from the laser diode 820 is coupled into the system through the polarizing beam splitter 819. Use of polarized light in various embodiments helps emphasize detection of light that underwent scattering inside the tissue and helps suppress contribution from light reflected from the surfaces.

The illumination beam from the laser diode 820 may be shaped to cover the area of tissue within the FOV. Light scattered from the tissue back and collected by lens 816 may be partially de-polarized, with the polarization component orthogonal to the incident beam reflected by the polarizing beam splitter 819 toward the collection unit 814. The collection unit 814, for example, may be a CCD camera. In such a polarization scheme, light reflected from the top of the tissue will not be significantly depolarized and therefore will not be reflected by the polarizing beam splitter 819 to the collection unit 814.

It may be noted that the resolution of a laser speckle imaging system is limited by the optical diffraction limit and the camera pixel size, as well as the average speckle size. Average speckle size scales inversely proportional to the NA of the lens system. Accordingly, the NA of the system may be configured to be relatively high to achieve a speckle size of roughly the same magnitude as the pixel resolution. In some embodiments, for example, the NA may range between about 0.2 and about 0.4. The optical magnification of an imager of the optical unit 818 may remain relatively low (e.g., a setting of 3-4× may resolve sub-10 micrometer features of a microvascular network in various embodiments). Generally, a linear magnification range between 1 and 5 may be used for typical sensors with pixel sizes ranging between about 2 and 10 micrometers.

The optical unit 818 may include electronically tunable optical power to provide focus adjustment for the system 800. Absorption-contrast images obtained via use of the incoherent light source 810 may be used to produce a focusing reference. Image contrast, variance, and entropy are examples of metrics that may be used to quantify image focus quality in various embodiments. Based on one or more measures of focus quality, an actuator signal may be generated to drive a tunable optical element of the optical unit 818 to maintain optimal or improved focus conditions.

It may be noted that, in laser speckle imaging, image capture parameters determine the speckle contrast, which is correlated with the blood flow velocity in the imaged vasculature. To capture a useful range of blood flow velocities, the collection unit 814 may be configured to operate at frame rates, for example, of 100 frames per second, 150 frames per second, or 200 frames per second, among others. The collection unit 814 may be configured to have an exposure time between 100 microseconds to 10 milliseconds in various embodiments. The collection unit 814, for example, may include a CCD chip.

Figure 9:
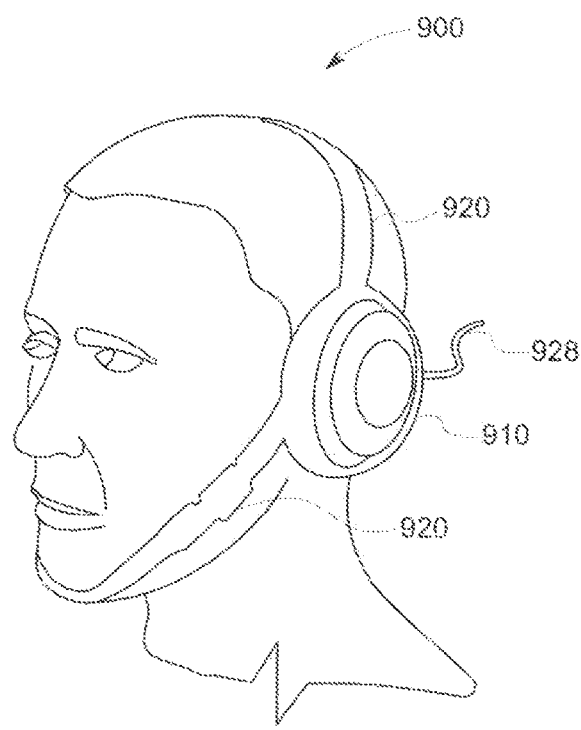
FIG. 9 is a schematic diagram of a sensing unit configured to be mounted to a patient in accordance with various embodiments.
Figure 10:
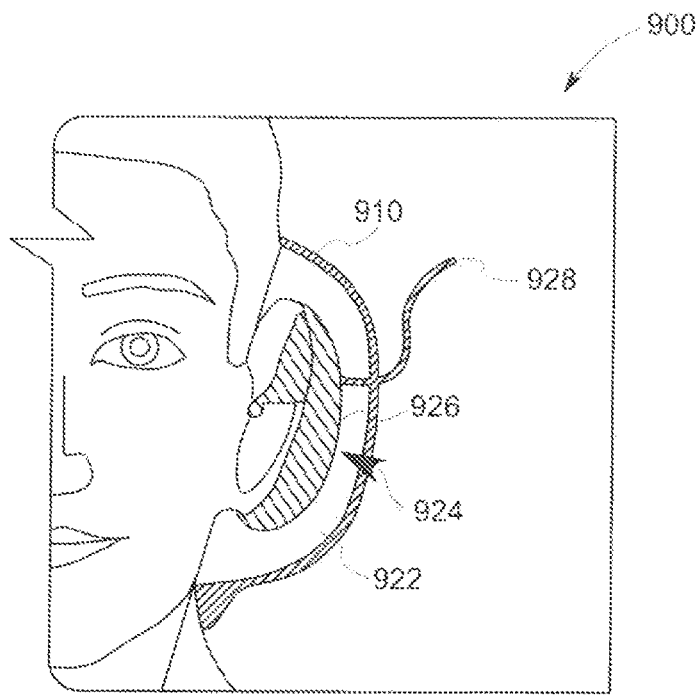
FIG. 10 illustrates a sectional view of the sensing unit of FIG. 9.

FIG. 9 illustrates a sensing unit 900 configured to be mounted to a patient, and FIG. 10 illustrates a sectional view of the sensing unit 900. The sensing unit 900 includes an earpiece 910 and, in some embodiments, a strap 920. The strap 920 may be flexible and/or adjustable and is configured to hold the earpiece 910 proximate to a patient's ear, thereby removing the need for an operator to attend to the sensing unit 900 and facilitating continuous and/or autonomous monitoring of microcirculation. The earpiece 910, as best seen in FIG. 10, includes a cushion 922, which may be formed with silicone and/or foam, that includes a cavity 924 therein. The earpiece 910 is an example of a non-invasive mounting structure configured for placement of a sensor proximate to the skin of a patient for detection of microcirculation. A sensor 926, sized and configured for placement in the cavity 924 and/or within or on an ear, provides illumination to the ear and collects imaging information from microvasculature within the ear. As the components are further miniaturized, the earpiece sensing unit may be further reduced to a self-supported ear insert eliminating or reducing the need for extra external cushioning, making the sensor even less intrusive for the patient. The sensor 926 is coupled to a processing unit and one or more light sources via cable 928. In various embodiments, blood flow in microvasculature of an ear observed transcutaneously via laser speckle imaging may provide a spatial resolution sufficient to resolve vessels in the ear having a thickness of about 10-20 micrometer. Generally, the ear of a patient may provide relatively easily detectable microcirculation flow as well as a convenient location for mounting a detector. Other locations of the patient (e.g., gums, palm of hand, or nasal mucosa) may be utilized in other embodiments.

Figure 11:
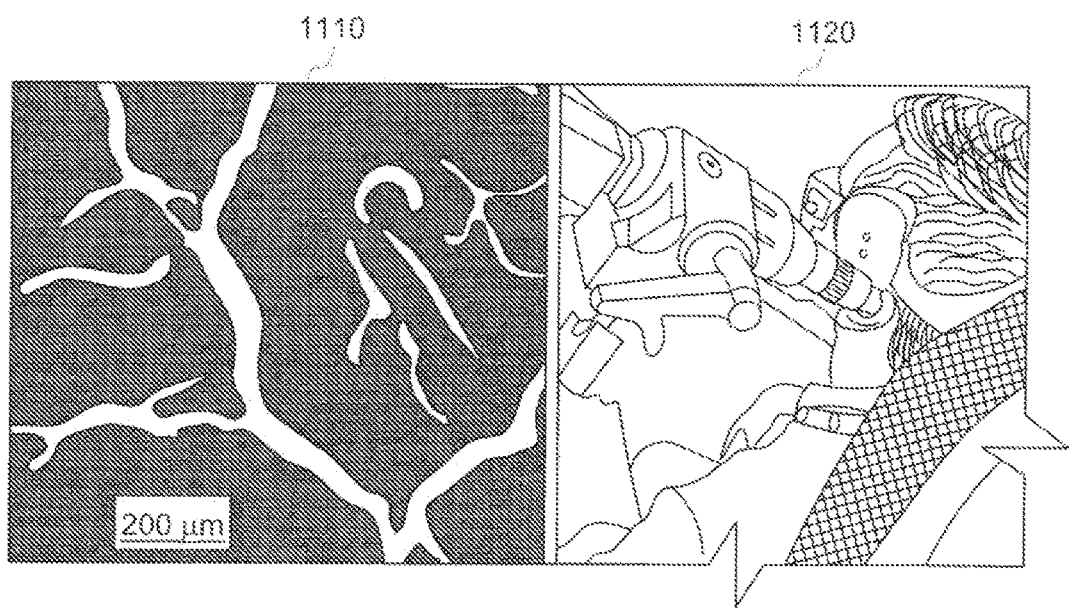
FIG. 11 depicts a measurement performed on a human ear.

Various tests have been performed demonstrating the utility of various aspects discussed herein. For example, FIG. 11 depicts a measurement performed on a human ear. View 1110 depicts an image of vasculature of a human ear obtained using a laboratory prototype depicted in view 1120. The measurement performed on the human ear showed small-sized vasculature having sufficient resolution to indicate that blood flow in small vasculature may be observed transcutaneously with LSI, maintaining high spatial resolution (e.g., 10 to 20 μm-thick vessels resolved for the ear.

Figure 12:
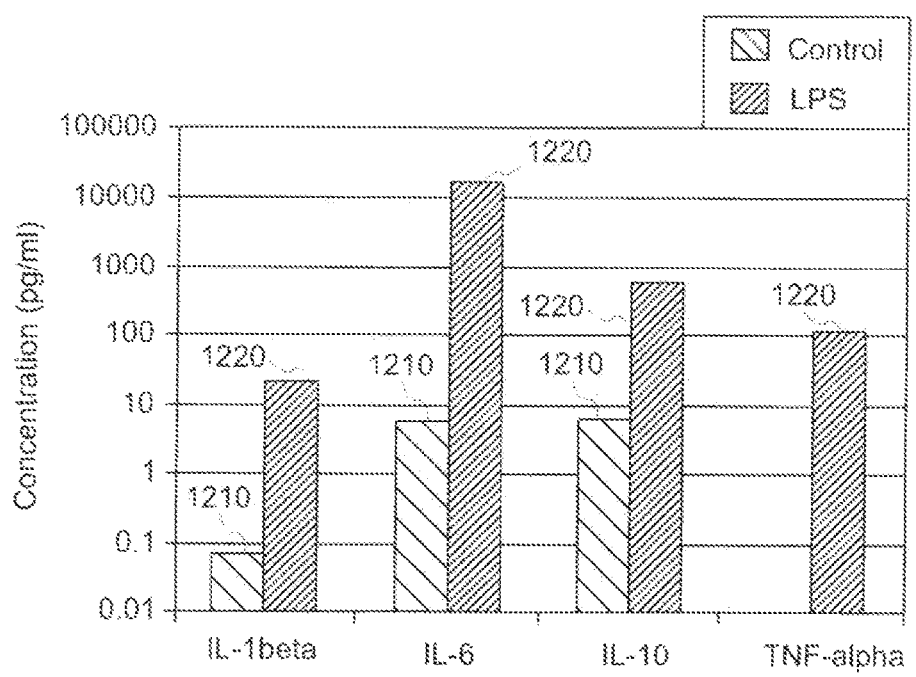
FIG. 12 depicts test results for measurements performed on mice.

Additional tests were performed using an established murine endotexemia model, using a lipopolysaccharide (LPS) intraperitoneal injection at 15 mg/kg). Animals were anesthetized with inhaled anesthetic and monitored for 1 to 2 hours starting at time points from 2 to 8 hours after the administration of LPS. Several measurement locations were tested, with the ear exhibiting the most distinct microvasculature. Measurements of the LPS-injected animal were contrasted with a negative control that did not receive LPS. The physiologic response to LPS was verified with an inflammatory cytokine panel test on blood plasma samples collected for each tested animal. Values of several cytokines known to respond to the inflammatory processes in sepsis are shown, for an LPS-treated and a control mouse, in FIG. 12. As seen in FIG. 12, the values 1210 for the control animals and the values 1220 for the LPS-injected animals differed. The LPS-injected animals showed significant increased levels of the cytokines, confirming the induced inflammatory response.

Figure 13:
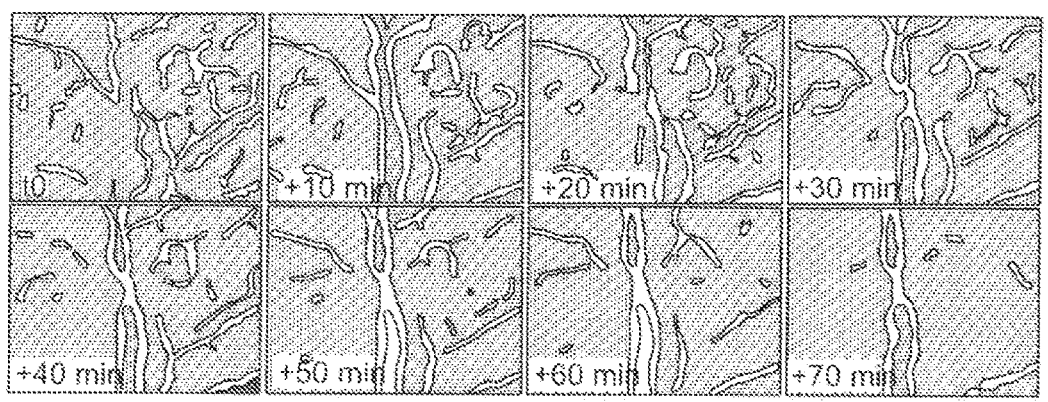
FIG. 13 depicts an image sequence of ear vasculature during a murine sepsis model experiment.

FIG. 13 depicts an image sequence of ear vasculature during a murine sepsis model experiment. As seen in FIG. 13, the endotoxemic animal showed a visually discernable change in the microvasculature pattern over the course of an approximately 1 hour experiment. A reduction of the number of vessels (<50 μm) is noticeable by the naked eye. It may be noted that such a decrease in flow in the smallest vessels is a physiologically expected effect of endotoxemia.

Figure 14:
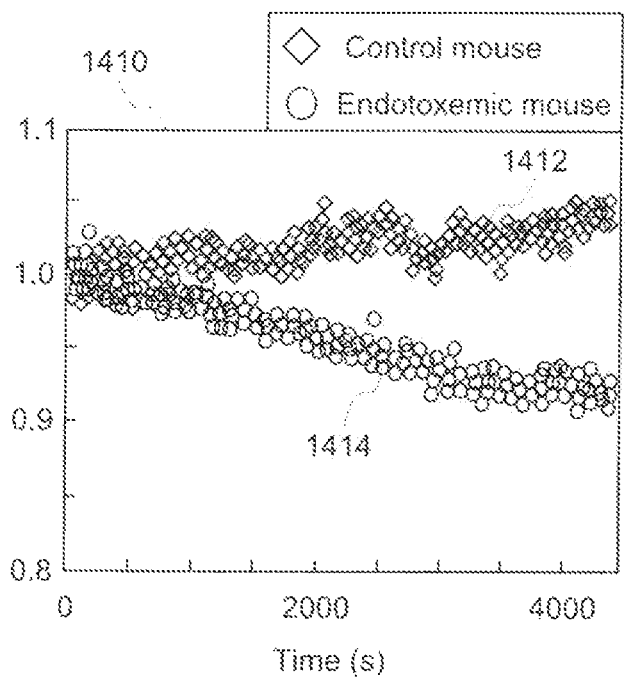
FIG. 14 depicts flow indices extracted from image sequences during a murine sepsis model experiment.
Figure 14:
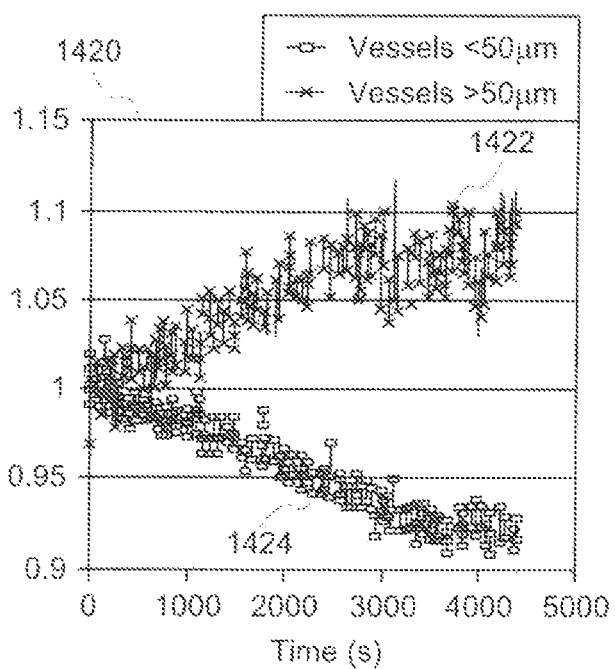

Using the results of murine measurements discussed above, various imaging processing approaches were used to generate a numerical index of microvascular flow. Due to the dynamic nature of the endotoxemic response, the focus of the example analysis was on identifying relative changes in the signal that showed a discernible trend in the LPS animals, and little change in the control animal. An automatic analysis method was utilized based on multi-scale Frangi vessel thickness filtering and histogram binning by vessel thickness. This analysis produced a numerical index of flow with only several seconds of integration, resulting in a continuous measurement as depicted in FIG. 14. View 1410 depicts flow indices over time, with an endotoxemic mouse index 1412 and a control mouse index 1414 plotted over time. View 1410 depicts overall perfused area for an endotoxemic mouse and for a control mouse. View 1420 depicts the trend in perfusion for small vessels (1424) and for large vessels (1422) for an endotoxemic mouse. As seen in view 1420, the index for large vessels increases over time while the index for small vessels decreases for the endotoxemic mouse, providing further confirmation that a laser speckle imaging based flow index may be utilized as an indicator of microvascular changes that occur in sepsis and septic shock.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
acquiring optical image information with a detection unit configured to be operably coupled to a patient, the optical image information corresponding to a microcirculation state of a tissue of the patient;
generating a sequence of microcirculation maps of microvasculature of the patient, at regular time intervals over a collection or monitoring period, using the optical image information;
extracting a plurality of Quantitative parameters from the optical image information, each quantitative parameter representing a property of the microcirculation state of the tissue;
generating a value of a quantitative microcirculation index based on at least one of the sequence of microcirculation maps and a value corresponding to each of the plurality of quantitative parameters, the quantitative microcirculation index corresponding to a static or a dynamic condition of the patient; and
continuously monitoring an existence or an onset or a progress of the condition of the patient using at least one of: a threshold value and a threshold rate, related to the value of the quantitative microcirculation index.

2. The method of claim 1, wherein the quantitative microcirculation index corresponds to a percentage of vessels that satisfy at least one size threshold.

3. The method of claim 1, wherein the quantitative microcirculation index corresponds to a ratio of a first group of vessels within a first size range to a second group of vessels within a second size range.

4. The method of claim 1, wherein the quantitative microcirculation index corresponds to at least one of an amount of change or a rate of change of a vessel size parameter.

5. The method of claim 1, further comprising providing laser energy to a region of interest of the patient, wherein acquiring the optical image information comprises collecting light emitted from the patient exposed to the laser energy, and wherein generating the microcirculation map is performed based on speckle patterns of the collected light.

6. The method of claim 1, wherein the detection unit comprises a non-invasive patient attachment configured to be attached to the patient, and wherein the optical image information is acquired continuously over a monitoring period.

7. The method of claim 1, further comprising acquiring auxiliary imaging information, and, before generating the microcirculation map, performing pre-processing on the optical image information using the auxiliary imaging information.

8. A system comprising:
a detection unit configured to be operably coupled to a patient and to acquire optical image information corresponding to a microcirculation state of a tissue of the patient; and
at least one processing unit configured to be operably coupled to the detection unit, and configured to:
generate a sequence of microcirculation maps of microvasculature of the patient at regular time intervals over a collection or monitoring period using the optical image information;
extract a plurality of quantitative parameters from the optical image information, each quantitative parameter representing a property of the microcirculation state of the tissue;
generate a value of a quantitative microcirculation index based on at least one of the sequence of microcirculation maps and a value corresponding to each of the plurality of quantitative parameters, the quantitative microcirculation index corresponding to a static or a dynamic condition of the patient; and
continuously monitor an existence or an onset or a progress of the condition of the patient using at least one of: a threshold value and a threshold rate, related to the quantitative microcirculation index.

9. The system of claim 8, wherein the quantitative microcirculation index corresponds to a percentage of vessels that satisfy at least one size threshold.

10. The system of claim 8, wherein the quantitative microcirculation index corresponds to a ratio of a first group of vessels within a first size range to a second group of vessels within a second size range.

11. The system of claim 8, wherein the quantitative microcirculation index corresponds to at least one of an amount of change or a rate of change of a vessel size parameter.

12. The system of claim 8, wherein the detection unit comprises a laser configured to provide laser energy to a region of interest of the patient and to collect light emitted from the patient exposed to the laser energy, and wherein the at least one processing unit is configured to generate the microcirculation map based on speckle patterns of the collected light.

13. The system of claim 8, wherein the detection unit comprises a non-invasive patient attachment configured to be attached to the patient.

14. The system of claim 13, wherein the non-invasive attachment comprises an ear-piece configured to be secured to the patient, and wherein the detection unit is configured to acquire the optical image information from a portion of an ear of the patient.

15. The system of claim 8, wherein the detection unit further comprises an incoherent light source and is configured to acquire auxiliary imaging information using the incoherent light source, and, wherein the at least one processor is configured to, before generating the microcirculation map, perform pre-processing on the optical image information using the auxiliary imaging information.

16. A tangible and non-transitory computer readable medium comprising one or more computer software modules configured to direct one or more processors to:
acquire optical image information via a detection unit configured to be operably coupled to a patient, the optical image information corresponding to A microcirculation state of a tissue of the patient;

generate a sequence of microcirculation maps of microvasculature of the patient at regular time intervals over a collection or monitoring period using the optical image information;

extract a plurality of quantitative parameters from the optical image information, each quantitative parameter representing a property of the microcirculation state of the tissue;

generate a value of a quantitative microcirculation index based on at least one of the sequence of microcirculation maps and a value corresponding to each of the plurality of quantitative parameters, the quantitative microcirculation index corresponding to a static or a dynamic condition of the patient; and continuously monitor an existence or an onset or a progress of the condition of the patient using at least one of: a threshold value and a threshold rate, related to the quantitative microcirculation index.

17. The computer readable medium of claim 16, wherein the quantitative microcirculation index corresponds to a percentage of vessels that satisfy at least one size threshold.

18. The computer readable medium of claim 16, wherein the quantitative microcirculation index corresponds to a ratio of a first group of vessels within a first size range to a second group of vessels within a second size range.

19. The computer readable medium of claim 16, wherein the quantitative microcirculation index corresponds to at least one of an amount of change or a rate of change of a vessel size parameter.

20. The computer readable medium of claim 16, wherein the computer readable medium is further configured to direct the one or more processors to control provision of laser energy to a region of interest of the patient, acquire information corresponding to light emitted from the patient responsive to the laser energy, and generate the microcirculation map based on speckle patterns of the collected light.

* * * * *